US010389340B2

(12) United States Patent
Nakagawa

(10) Patent No.: US 10,389,340 B2
(45) Date of Patent: Aug. 20, 2019

(54) DELAY CIRCUIT, ELECTRONIC CIRCUIT USING DELAY CIRCUIT AND ULTRASONIC IMAGING DEVICE

(71) Applicant: Hitachi, Ltd., Chiyoda-ku, Tokyo (JP)

(72) Inventor: Tatsuo Nakagawa, Tokyo (JP)

(73) Assignee: HITACHI, LTD., Tokyo (JP)

( * ) Notice: Subject to any disclaimer, the term of this patent is extended or adjusted under 35 U.S.C. 154(b) by 636 days.

(21) Appl. No.: 14/773,275

(22) PCT Filed: Mar. 28, 2013

(86) PCT No.: PCT/JP2013/059412
§ 371 (c)(1),
(2) Date: Sep. 4, 2015

(87) PCT Pub. No.: WO2014/155635
PCT Pub. Date: Oct. 2, 2014

(65) Prior Publication Data
US 2016/0013782 A1 Jan. 14, 2016

(51) Int. Cl.
*H03K 5/00* (2006.01)
*H03K 5/133* (2014.01)
(Continued)

(52) U.S. Cl.
CPC .......... *H03K 5/133* (2013.01); *A61B 8/4494* (2013.01); *A61B 8/54* (2013.01); *G01S 7/5208* (2013.01);
(Continued)

(58) Field of Classification Search
CPC ............. G01S 15/8927; G01S 7/52025; G01S 7/5208; G10K 11/346; G11C 27/00;
(Continued)

(56) References Cited

U.S. PATENT DOCUMENTS 4,769,612 A * 9/1988 Tamakoshi ........... H03H 19/004
327/554
5,123,415 A 6/1992 Daigle
(Continued)

FOREIGN PATENT DOCUMENTS

JP 56-129419 A 10/1981
JP 62-123819 A 6/1987
(Continued)

OTHER PUBLICATIONS

European Search Report dated Jan. 31, 2017 for related European Application No. 13879941.6.
(Continued)

*Primary Examiner* — Mark D Remaly
(74) *Attorney, Agent, or Firm* — Miles & Stockbridge PC

(57) ABSTRACT

A delay circuit and an ultrasonic imaging apparatus with the higher-accuracy delay time, the longer maximum delay time, and the lower power consumption are provided. An input line to which an analog input signal is input, a plurality of analog signal memory devices, an output line, a plurality of sampling switches that control connection/disconnection between the input line and the plurality of analog signal memory devices, a plurality of output switches that control connection/disconnection between the plurality of analog signal memory devices and the output line, and a clock generation part that generates sampling switch control signals for controlling the sampling switches and output switch control signals for controlling the output switches are provided, and phase of the sampling switch control signals may be shifted with respect to phase of the output switch control signals.

14 Claims, 11 Drawing Sheets

(51) Int. Cl.
*H03H 19/00* (2006.01)
*H03H 11/26* (2006.01)
*G11C 27/02* (2006.01)
*A61B 8/00* (2006.01)
*G11C 27/00* (2006.01)
*G01S 7/52* (2006.01)
*G01S 15/89* (2006.01)
*G10K 11/34* (2006.01)

(52) U.S. Cl.
CPC ...... *G01S 7/52025* (2013.01); *G01S 15/8927* (2013.01); *G10K 11/346* (2013.01); *G11C 27/00* (2013.01); *G11C 27/024* (2013.01); *H03H 11/265* (2013.01); *H03H 19/00* (2013.01); *H03K 2005/00019* (2013.01)

(58) Field of Classification Search
CPC .... G11C 27/024; H03H 11/265; H03H 19/00; H03K 2005/00019; H03K 5/133; A61B 8/4494; A61B 8/54
See application file for complete search history.

(56) References Cited

U.S. PATENT DOCUMENTS

| | | | |
|---|---|---|---|
| 5,217,017 | A | 6/1993 | Matsushima |
| 6,061,279 | A | 5/2000 | Toda et al. |
| 2004/0251946 | A1 | 12/2004 | Miyagi |
| 2009/0067555 | A1* | 3/2009 | Hosoya ............... G11C 27/024 375/344 |

FOREIGN PATENT DOCUMENTS

| | | | |
|---|---|---|---|
| JP | 62-179437 | A | 8/1987 |
| JP | 4-232888 | A | 8/1992 |
| JP | 5-7587 | A | 1/1993 |
| JP | 05-034412 | A | 2/1993 |
| JP | 7-308319 | A | 11/1995 |
| JP | 10-173498 | A | 6/1998 |
| JP | 11-260093 | A | 9/1999 |
| JP | 2004-279155 | A | 10/2004 |
| JP | 2011-250946 | A | 12/2011 |
| WO | WO 03/043190 | A1 | 5/2003 |

OTHER PUBLICATIONS

International Search Report from International Patent Application No. PCT/JP2013/059412, dated May 7, 2013.

* cited by examiner

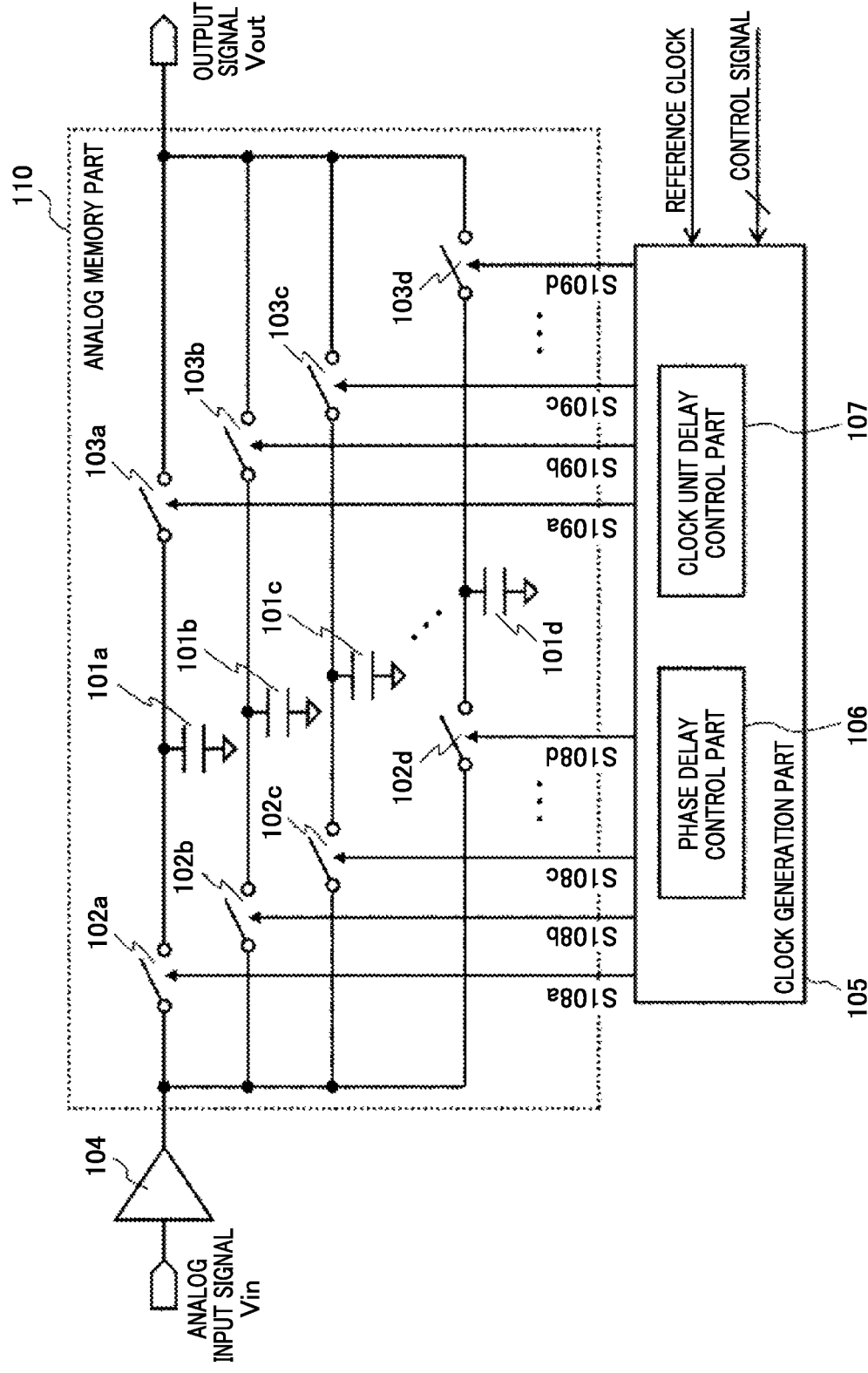

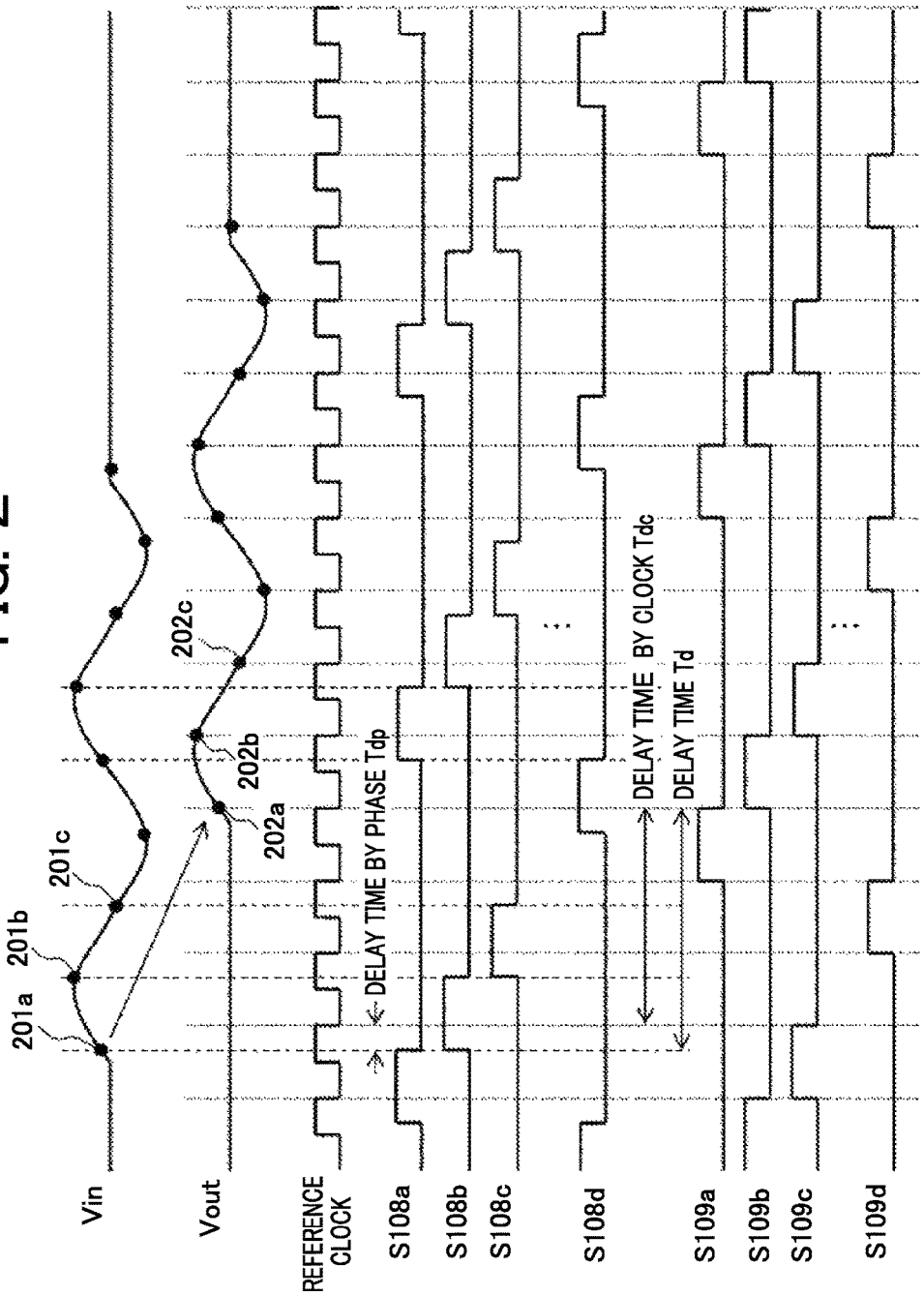

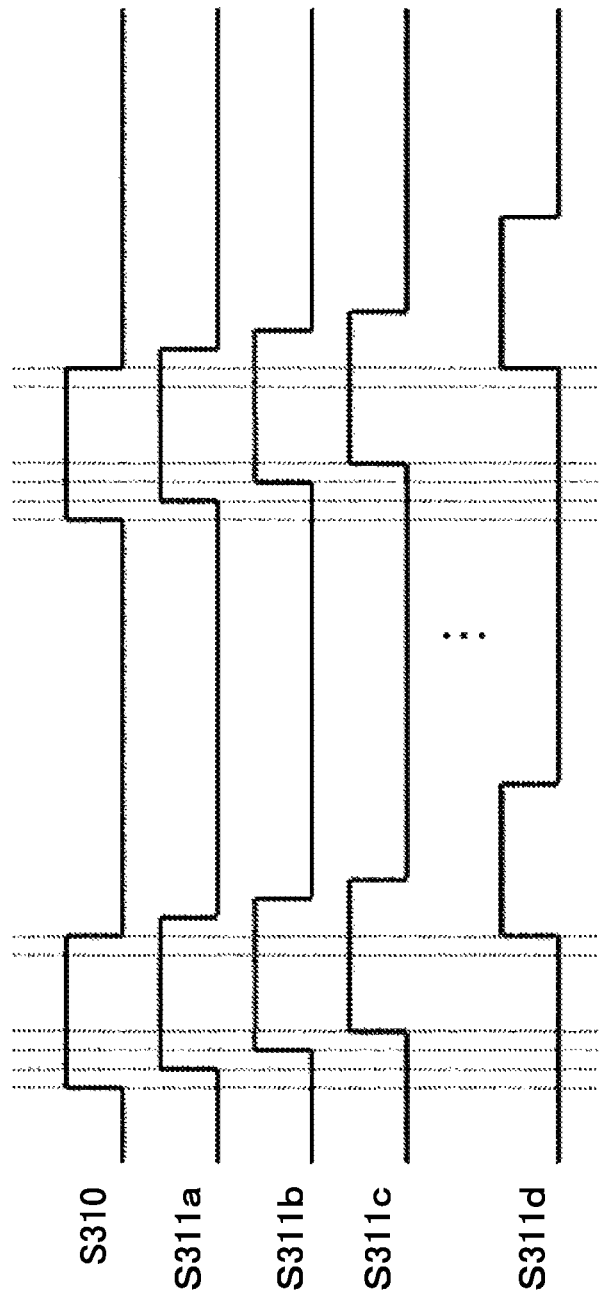

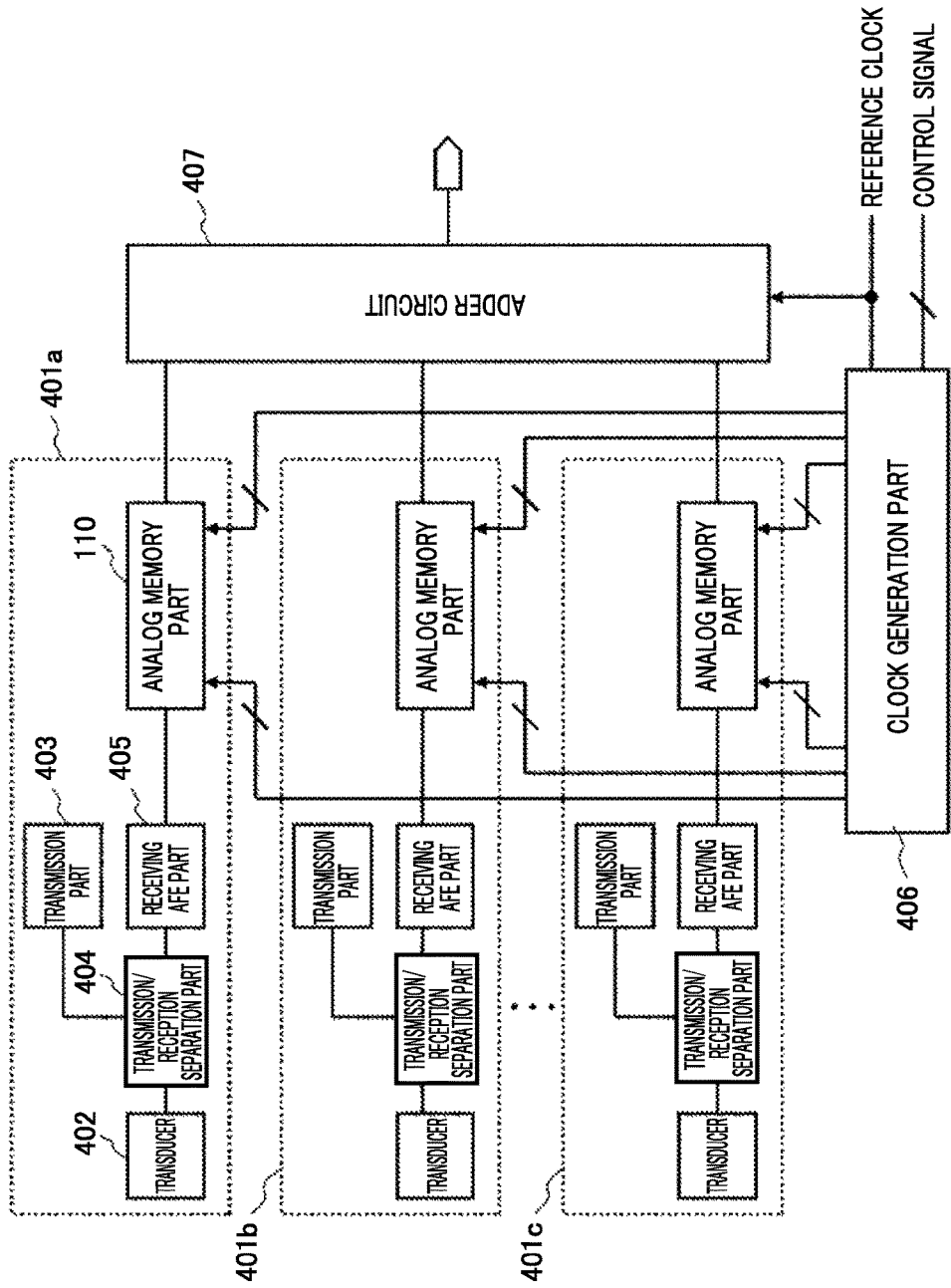

DELAY CIRCUIT, ELECTRONIC CIRCUIT USING DELAY CIRCUIT AND ULTRASONIC IMAGING DEVICE

TECHNICAL FIELD

This invention relates to a delay circuit, an electronic circuit and an ultrasonic imaging apparatus using the same, and specifically to a delay circuit that generates small delays for analog signals, an electronic circuit using the same, and an ultrasonic imaging apparatus including the electronic circuit.

BACKGROUND ART

Ultrasonic imaging apparatuses play an important role in current medical care. This is because the apparatuses are smaller in scale than other medical diagnostic imaging apparatus including X-ray diagnostic apparatuses and MRI (Magnetic Resonance Imaging) apparatuses, and the apparatuses can display e.g. motions of objects to be inspected such as pulsing motions of hearts and motions of fetuses in real time by simple operation of only applying ultrasonic probes to body surfaces.

Specifically, the ultrasonic imaging apparatus respectively supplies drive signals to a plurality of vibrating elements contained in the ultrasonic probe, and thereby, transmits ultrasonic wave into a test object. Then, the ultrasonic imaging apparatus respectively receives reflected wave of the ultrasonic wave generated by differences in acoustic impedance among living tissues by the plurality of vibrating elements, and generates an ultrasonic image based on the reflected wave received by the ultrasonic probe.

Here, in the ultrasonic imaging apparatus, to improve image quality of the ultrasonic image, control of delay times is performed on drive signals supplied to the plurality of vibrating elements and reflected wave signals respectively obtained from the plurality of vibrating elements.

Specifically, the ultrasonic imaging apparatus controls times of the drive signals supplied to the respective vibrating elements using the delay times in response to distances between a predetermined focal point within the test object and the respective vibrating elements, and thereby, transmits ultrasonic wave beam-formed on the predetermined focal point of the test object. Then, the ultrasonic imaging apparatus synchronizes and adds (phases and adds) the signals from the predetermined focal point received at different times in the respective vibrating elements using the delay times in response to the distances between the predetermined focal point within the test object and the respective vibrating elements. Thereby, the ultrasonic imaging apparatus generates one focused received signal.

As described above, in order to synchronize the respective signals from the predetermined focal point, an analog or digital delay circuit is required. For example, PTL 1 discloses a configuration for delaying by series-connecting sample holding means and a plurality of capacitor memory circuits, and, at a constant sample frequency, delaying with respect to each sampling cycle in the capacitor memory circuits and controlling a hold time of the sample holding means for shorter delays equal to or less than the sampling cycle. Further, PTL 2 discloses an ultrasonic diagnostic apparatus that performs reception delay time control by digital processing for reducing a circuit scale and manufacturing cost.

CITATION LIST

Patent Literatures

PTL 1: JP-A-62-123819
PTL 2: JP-A-2011-250946

SUMMARY OF INVENTION

Technical Problems

In order to obtain a three-dimensional stereoscopic image, not a two-dimensional tomographic image, in a two-dimensional probe in which vibrators (transducers) are arranged in a two-dimensional array, several thousands to ten thousand channels of vibrators are used. In the two-dimensional probe, it is impractical to connect all vibrators to a main body unit in view of limitations of the number of cables, and handling for reducing the number of channels is required within the probe head. Therefore, an electronic circuit that delays and adds analog signals is required.

Further, in a one-dimensional probe, analog signals are delayed and added, and thereby, the number of cables and the number of analog/digital converters may be reduced and cost reduction and downsizing may be realized. Accordingly, an electronic circuit that delays and adds analog signals is required.

When a circuit that delays analog signals is provided within the probe head, it is necessary to make power consumption of the circuit lower. This is because it is necessary to suppress temperature rise due to heat generation in the probe head. Further, in order to accurately focus received beams in the respective vibrators, the higher resolution of delay times for delaying the signals is required. Further, the longer maximum delay time is required.

For a delay circuit using analog sampling in related art, there is a method of parallel-connecting a plurality of capacities, sequentially sampling signals in the capacities, and sequentially reading the signals from the capacities after predetermined delay times. However, the delay resolution of the circuit is determined by the clock frequency for sampling and it is necessary to raise the clock frequency for higher resolution, and there is a problem of increase in power consumption. Further, the maximum delay time is determined by the clock frequency and the number of parallel-connected capacities and the higher resolution and the maximum delay time have a trade-off relationship, and it is necessary to parallel-connect so many capacities for meeting both.

As described in PTL 1, a circuit that generates small delays and a circuit that generates coarse delays are series-connected, and thereby, a delay circuit with the higher resolution and the longer maximum delay time may be formed. However, when multiple circuits are connected, power consumption of the respective circuits is added and power consumption as a whole increases.

Further, the small delays are generated by control of the hold times of the sample holding means, and thereby, the hold times vary depending on the delay times and characteristics of analog signals are deteriorated. This is caused by changes in amount of leak of the charge charged in the capacities depending on the hold times. As a result, distortion and offset dependent on the hold times are caused in the held signals, and the circuit characteristics are deteriorated.

Furthermore, it is necessary to take a sufficient hold time for the downstream circuit to receive the signal, and, to generate a small delay time, it is impossible to take the sufficient hold time and the characteristics are deteriorated. Specifically, for example, the transient response in holding is not converged, but ringing is caused. The ringing may cause an error when the downstream circuit performs sampling. To avoid this, the operating frequency of the circuit is eventually raised, and there is a problem of increase in power consumption.

In addition, in the ultrasonic imaging apparatus, it is necessary to add the signals from the plurality of vibrators after delaying of the analog signals, however, synchronization among the plurality of channels in this regard is not considered in PTL 1.

In light of the situations, an object of the invention is to provide a delay circuit with the higher resolution, the longer maximum delay time, and the lower power consumption and an ultrasonic imaging apparatus using the circuit.

The above described and other objects and new characteristics of the invention will be clear from the description and accompanying drawings of the specification.

Solution to Problems

In order to solve the above described problems, the invention employs a configuration described in Claims.

This application includes a plurality of means for solving the problems, and an example thereof is a delay circuit including an input line to which an analog input signal is input, a plurality of analog signal memory devices, an output line from which an analog output signal is output, a plurality of sampling switches that control connection/disconnection between the input line and the plurality of analog signal memory devices, a plurality of output switches that control connection/disconnection between the plurality of analog signal memory devices and the output line, and a clock generation part that generates sampling switch control signals for respectively controlling the plurality of sampling switches and output switch control signals for respectively controlling the plurality of output switches from a reference clock, the delay circuit delaying signals by controlling the plurality of sampling switches to accumulate the analog input signal in the plurality of analog signal memory devices and controlling the plurality of output switches to output the signals accumulated in the plurality of analog signal memory devices to the output line, wherein phase of the plurality of sampling switch control signals may be shifted with respect to phase of the plurality of output switch control signals.

Advantageous Effects of Invention

According to the invention, a delay circuit with a higher-accuracy delay time, the longer maximum delay time, and the lower power consumption and an ultrasonic imaging apparatus using the circuit may be provided.

BRIEF DESCRIPTION OF DRAWINGS

FIG. 1 is a configuration diagram of a delay circuit according to Example 1 of the invention.

FIG. 2 is a timing chart for explanation of an operation of the delay circuit according to Example 1 of the invention.

FIG. 3B is a timing chart of internal signals of the clock generation part.

FIG. 4 is a configuration diagram of an electronic circuit used for an ultrasonic imaging apparatus according to Example 2 of the invention.

DESCRIPTION OF EMBODIMENTS

Figure 3A:
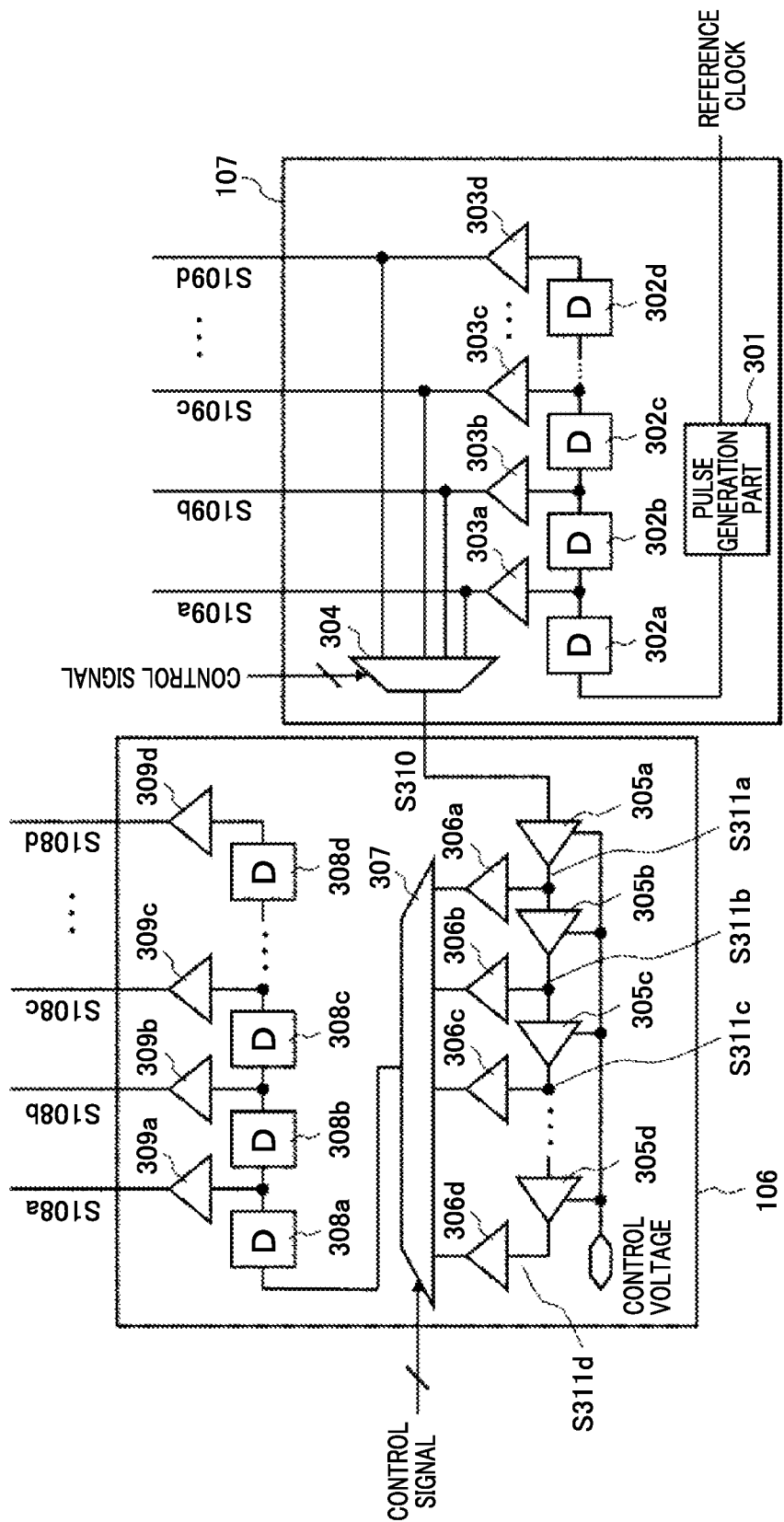
FIG. 3A is a configuration diagram of a clock generation part according to Example 1 of the invention.

Embodiments for implementing the invention will be explained with reference to the drawings. Note that, in all drawings for explanation of the embodiments for implementing the invention, the same names and signs are assigned to the elements having the same functions and their repetitive explanation will be omitted.

Example 1

A delay circuit according to Example 1 of the invention is explained using FIGS. 1 to 3. FIG. 1 is a configuration diagram of the delay circuit according to Example 1 of the invention. The circuit includes capacities $101a$, $101b$, $101c$, . . . , switches $102a$, $102b$, $102c$, . . . , switches $103a$, $103b$, $103c$, . . . , a buffer 104, a clock generation part 105. The clock generation part 105 has a phase delay control part 106 and a clock unit delay control part 107. Note that the indices a, b, c, . . . show the same configuration elements and are omitted when not particularly necessary.

An analog input signal Vin is amplified or impedance-converted by the buffer 104, and then, input from an input line to the capacities 101 via the switches 102 and charge corresponding to the analog signal Vin is accumulated therein. The charge accumulated in the capacities 101 is output as an output signal Vout from an output line via the switches 103. The times when the signal is charged in the capacities 101 are controlled by the switches 102, and the times when the signals are output from the capacities 101 are controlled by the switches 103. The clocks for controlling these switches are generated in the clock generation part 105. In the delay generation circuit of the example, a plurality of capacities are parallel-connected, and an operation of sampling and sequentially storing the analog input signal Vin in the capacities and sequentially outputting the stored signals after a predetermined time is performed.

FIG. 2 is a timing chart for explanation of an operation of the delay generation circuit according to Example 1 of the invention. The switch $102a$ is controlled by a clock signal S$108a$. Here, when the clock signals S108 are at a high level, the switches 102 are on, however, the polarity is not limited. When the switch $102a$ is on, charge corresponding to the analog input signal is accumulated in the capacity $101a$. The value of the analog input signal at the time when the switch $102a$ changes from on to off is accumulated in the capacity $101a$ ($201a$). The charge accumulated in the capacity $101a$ is output to an output signal when the switch 103a is on (202a). The times when the switch 103a is turned on/off are controlled by a clock signal S109a. That is, the signal sampled in the capacity 101a by the clock signal S108a is output to the output signal at the time when the clock signal S109a is turned on.

Similarly, in the other parallel-arranged capacities 101a, 101b, 101c, . . . , charge corresponding to the analog input signal Vin is accumulated at the respective times of the clock signals S108b, S108c, . . . , and signals corresponding to the accumulated charge are output at times when the clock signals S109b, S109c, . . . are turned on.

As described above, the signals sampled at the clock signals S108 are output at the clock signals S109, and the signals delayed by the amounts of delay times of the clock signals S108 and the clock signals S109 compared to the analog input signal Vin are output to the output signal Vout.

The delay times of the clock signals S108 and the clock signals S109 are controlled by the phase delay control part 106 and the clock unit delay control part 107 of the clock generation part 105. In the clock unit delay control part, with a clock cycle Tclk of the reference clock as a unit, a delay time of an integral multiple thereof is controlled. That is, a delay time Tdc=M·Tclk by the clock is generated. Here, M is an integer number.

Further, in the phase delay control part 106, a small delay time Tdp less than the clock cycle Tclk is generated. The small delay time Tdp is generated by control of the phase of the clock signal. Therefore, a total delay time Td=Tdp+Tdc=Tdp+M·Tclk. The resolution of the delay time is determined by resolution that can control the phase delay Tdp. For example, if the clock of the phase divided into eight with respect to the clock cycle is generated and controlled, the resolution of one-eighth of the clock cycle, i.e., Tclk/8 is obtained. Further, the maximum delay time is determined by the clock cycle and the number of parallel-connected capacities. Therefore, the longer delay time may be accurately obtained. In this manner, the phase delay and the clock unit delay are combined, and thereby, both the higher accuracy of the delay time may be compatible with the longer maximum delay time.

As a method of raising the resolution of the delay time, shortening of the clock frequency Tclk is considered. However, if the clock frequency Tclk is made shorter, the frequency at which charging and discharging in the capacity is higher, and power consumption increases. Further, the maximum value of the delay time is determined by the number of parallel-connected capacities and the clock cycle. To raise the resolution of the delay time, if the maximum delay time is secured while the clock cycle is made shorter, it is necessary to parallel-connect the larger number of capacities by the amount. Accordingly, the area also increases.

As in the example, when the small delay Tdp is generated by control of the phase of the clock signal, the resolution of the delay time can be raised without raise of the clock frequency. Therefore, a delay circuit with higher accuracy and lower power consumption may be provided. Further, the maximum delay time is determined by the number of parallel capacities and the clock cycle, and thereby, the area increase may be suppressed.

FIG. 3A shows an example of a configuration of the clock generation part 105. The clock generation part includes the clock unit delay control part 107 and the phase delay control part 106. The clock unit delay control part 107 includes a pulse generation part 301, delay elements 302a, 302b, . . . , buffers 303a, 303b, . . . , and a selector 304. The phase delay control part 106 includes buffers 305a, 305b, . . . , buffers 306a, 306b, . . . , a selector 307, delay elements 308a, 308b, . . . , and buffers 309a, 309b, . . . .

The pulse generation part 301 generates a pulse signal that outputs a high level for one cycle in a plurality of cycles with the reference clock as a unit. Specifically, for example, when the number of parallel capacities 101 is N, the part outputs a pulse signal in a cycle N times the cycle of the reference clock. The pulse signal generated in the pulse generation part 301 is delayed by each clock cycle in the delay elements 302a, 302b, . . . arranged in series. The delayed signals are used for control of the switches 103a, 103b, . . . as the clock signals S109a, S109b, . . . via the buffers 303a, 303b, . . . .

Further, the clock signals S109a, S109b, . . . are input to the selector 304 and one clock signal of them is selected in response to a control signal. The delay in units of clocks is set by a signal S310 selected by the selector 304.

The signal S310 selected by the selector 304 is input to the series-connected buffers 305a, 305b, . . . . FIG. 3B is a timing chart of internal signals of the clock generation part 105. The buffer 305 has a delay time controlled by a control voltage, and has a role of shifting the phase of the clock. The buffer is formed as e.g. a circuit in which inverters that output output signals inverted to the input signals are arranged in series. The signal S310 selected by the selector 304 is input to the buffers 305 and signals S311a, S311b, . . . with phase shifted little by little are output to the respective buffers 305a, 305b, . . . . The signals S311 with phase shifted little by little are input to the selector 307 via the buffers 306a, 306b, . . . .

The amount of phase shift by the buffer 305 is set to an amount of one cycle of the reference clock or less, and thereby, the small delay time may be arbitrarily set. Further, the delay time of the single buffer 305 is resolution of the delay time that can be set by the delay circuit of the example.

In the selector 307, one of the signals S311 with phase shifted little by little is selected. The delay time equal to or less than the clock cycle is generated by the signal selected by the selector 307. The output signal of the selector 307 is delayed by the clock cycle by the series-connected delay elements 308a, 308b, . . . . The delayed signals are used for control of the switches 102a, 102b, . . . as the clock signals S108a, S108b, . . . via the buffers 309a, 309b, . . . .

In this manner, with respect to the clock signals S109 generated from the reference clock, the delay time in units of clocks is selected by the selector 304 and the signal with phase shift is selected by the selector 307. According to the circuit configuration, the delay time with higher resolution may be generated by control of the phase of the clock.

As the ultrasonic imaging apparatus, when e.g. ultrasonic wave in the frequency band from 2 to 8 MHz is used, the sampling at a frequency of twice the frequency or more is necessary. Therefore, as the frequency of the reference clock, the clock at 16 MHz or more, e.g. 20 MHz is used. In this case, the clock signal having phase with a period divided into eight is generated, a delay circuit having resolution of 6.25 ns may be provided.

According to the configuration like the example, most of the circuit generating delay times may be implemented by digital circuits. Generally, compared to an analog circuit, a digital circuit has lower power consumption because it does not consume stationary current. In the case where an analog circuit that generates small delays and an analog circuit that generates large delays are series-connected, a delay circuit with the higher resolution and the longer maximum delay time may be realized, however, power consumption increases with the increase of the number of series-connected circuits because the respective analog circuits consume power. In the delay circuit of the example, delay times with the higher accuracy and the longer maximum delay time are generated by the digital circuits, and it is not necessary to series-connect multiple analog circuits for charging and discharging in the capacities. Therefore, the lower power consumption of the delay circuit of the example can be realized compared to the case where multiple analog circuits are series-connected.

Note that, in the example, the explanation is made with the cycle of the reference clock as a unit, however, not limited to that. A half of the reference clock Tclk/2 may be used as a unit.

When the delay time is generated by control of the phase of the clock as in the example, the phase of the clock signal S108 is shifted by one cycle at the maximum with respect to the phase of the reference clock. Accordingly, when the delay of the clock unit is set, a range in which setting is disabled is provided on the assumption that the phase is shifted by one cycle due to phase shift. That is, regardless of the value of the phase of the clock signal S108, control is performed so that the time when the clock signal S108 is on and the time when the clock signal S109 is on may not overlap. Thereby, the maximum delay time is shorter by one cycle of the reference clock, and the number of parallel-arranged capacities is set in consideration of that.

If only the phase of the clock for sampling is shifted, for example, a method of setting the time of rising with the same phase as the reference clock and changing the time of falling, i.e., changing the duty ratio is considered. However, if the duty ratio is changed, the time when the clock is on at sampling changes depending on the delay time, and an error in gain at sampling of analog signals or the like is caused. Therefore, it is desirable that the phase is shifted with little change of the period in which the clock signal is high.

Note that, in the example, the configuration in which the capacity is used as an element for storing an analog signal and the analog signal is stored using charge accumulated in the capacity is explained, however, not limited to that. For example, an analog signal may be stored as a current using a transistor such as a MOS. When an analog signal is stored as a current, compared to the case of the capacity, there is an advantage that the occupied area may be reduced, though power consumption is higher.

Example 2

A plurality of the delay circuits described in Example 1 are used for an ultrasonic imaging apparatus. The example in this case is explained using FIG. 4. FIG. 4 is a configuration diagram of an electronic circuit used for an ultrasonic imaging apparatus of Example 2 of the invention. The circuit includes single-element circuits 401a, 401b, . . . , a clock generation part 406, and an adder circuit 407. The single-element circuit 401 includes a transducer 402, a transmitting part 403, a transmission/reception separating part 404, a receiving analog front end part (AFE) 405, and an analog memory part 110.

The signal output from the transmitting part 403 passes through the transmission/reception separating part 404 and is provided to the transducer 402. An ultrasonic signal is output from the transducer 402. Further, an ultrasonic signal reflected is received by the transducer 402, passes through the transmission/reception separating part 404 and is input to the receiving AFE part 405. In the receiving AFE part 405, processing of amplification, filtering, etc. is performed on the received signal. The output of the receiving AFE part 405 is input to the analog memory part 110. The analog memory part 110 is e.g. the circuit shown in FIG. 1, and samples and accumulates an analog input signal in a memory based on a clock signal from a clock generation part 406, and outputs the signal after a predetermined delay time.

The delay times provided to the analog memory parts 110 of the respective channels are controlled by the clock signals generated by the clock generation part 406. For the clock signals for controlling the switches 103 for output of the analog memory part 110, clocks synchronized with the same phase among the respective channels are used. Accordingly, the outputs of respective channel circuits 401a, 401b, . . . are input to the adder circuit 407 as the signals with the same phase and the signals are added. On the other hand, the sampling switches 102 of the analog memory part 110 generate small delay times, and signals with phase shifts among the respective channels may be formed. As described above, the clocks for controlling the output switches of the analog memories are in phase among the channels, and thereby, the signals input to the downstream adder circuit 407 are signals in phase among the respective channels. In this manner, even when high-accuracy delay times are generated with phase differences of clocks, the phase of the output signals may be made the same and the influence of the controlled phase may be eliminated in the downstream circuit operations.

A low-pass filter may be provided for the output signals of the respective delay circuits. For example, if a filter that may remove noise of the clock cycle is used, the noise of the clock cycle may be removed. Further, a similar low-pass filter may be provided for the output of the adder circuit.

Note that it is not necessary to add outputs of all channels in the adder circuit, but the outputs may be divided into a plurality of blocks and respectively added. For example, in the case of 192 channels, groups of four channels are added and 48 outputs after addition may be obtained. Or, the signals of the two-dimensional array of the 8192 channels may be added by 64 channels in 8×8 array, and 128 outputs may be obtained. The signals are connected from the probe to the main body and transmitted by cables.

As described above, the signals of the plurality of channels are delayed with higher accuracy and added, and thereby, the number of output signals may be reduced compared to the number of elements of the transducers. Thereby, the number of cables may be reduced and the number of A/D converters that convert analog signals into digital signals may be reduced, and thus, the lower cost may be realized. Further, in the two-dimensional transducer array, it is not practical that the signals of all channels are connected from the probe to the main body, however, the signals are delayed with higher accuracy and added as in the example, and thereby, the probe and the main body can be connected with the practical number of cables.

Example 3

Figure 5:
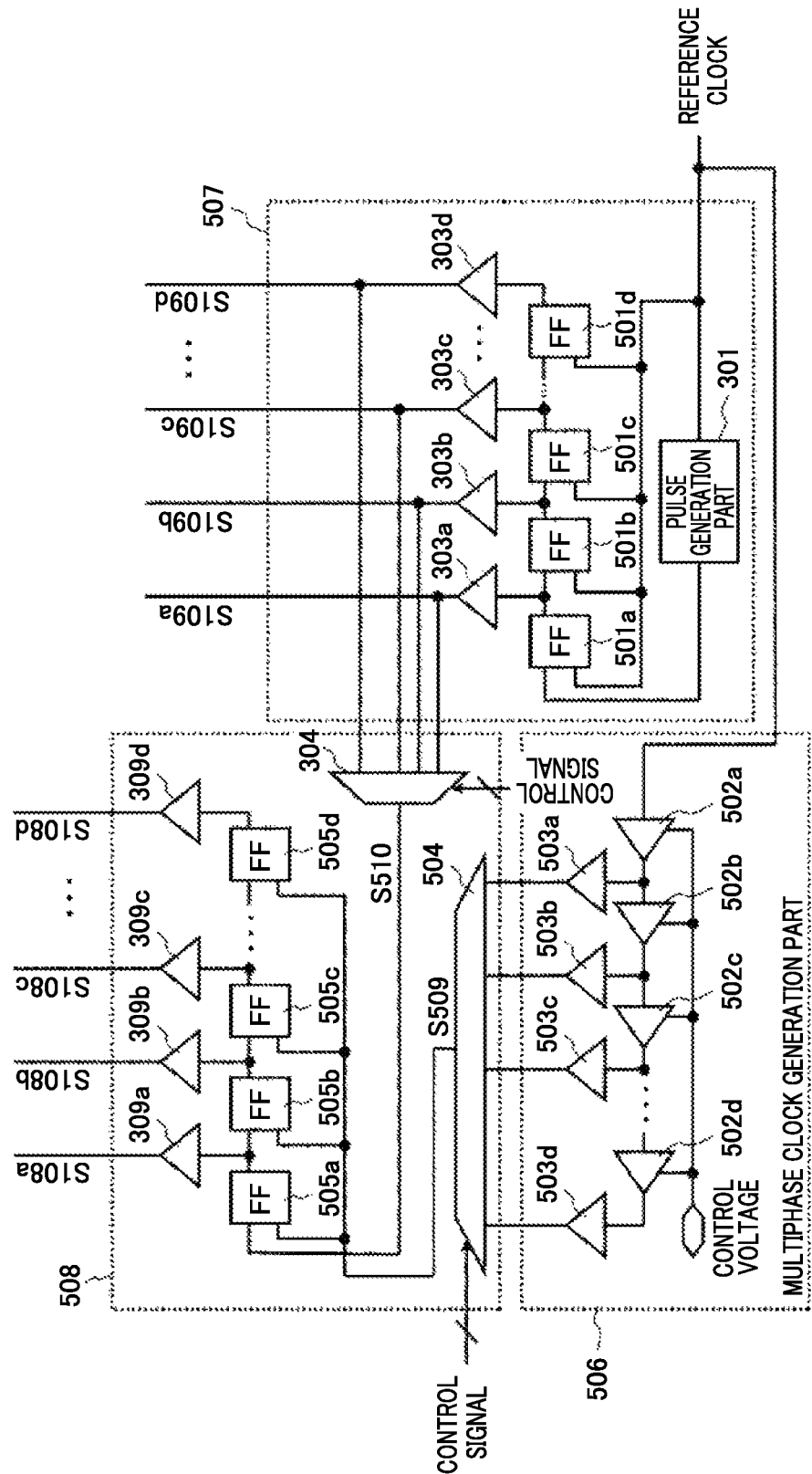
FIG. 5 is a configuration diagram of a clock generation part according to Example 3 of the invention.

In the example, another configuration of the clock generation part is explained. FIG. 5 is a configuration diagram of a clock generation part according to Example 3 of the invention. The clock generation part includes a multiphase clock generation part 506, an output clock generation part 507, and a sampling clock generation part 508. The output clock generation part 507 includes a pulse generation part 301, flip-flops (FFs) 501a, 501b, . . . , and the buffers 303a, 303b, . . . . The multiphase clock generation part 506 includes buffers 502a, 502b, . . . and buffers 503a, 503b, . . . . The sampling clock generation part 508 includes the selector 304, a selector 504, flip-flops 505a, 505b, ..., and the buffers 309a, 309b, .... The multiphase clock generation part 506 is a circuit that generates a multiphase clock with phase shifts with reference to the reference clock. The output clock generation part 507 is a circuit that generates the clock signals S109 for controlling the output switches of the analog memory part. Further, the sampling clock generation part 508 is a circuit that generates the clock signals S108 for controlling sampling switches of the analog memory part.

In the pulse generation part 301, a pulse signal at a high level for one cycle within a plurality of cycles of the reference clock is generated. In the FFs 501, the pulse signals are synchronized with the reference clock signal and latched, and delayed by one clock. The delayed signals control the output switches 301 of the analog memory part as the clock signals S109 via the buffers 303. Further, the clock signals S109 are input to the selector 304.

The multiphase clock generation part 506 generates a multiphase clock with phase shifts with reference to the reference clock. Specifically, the reference clock is input to the multiple buffers 502 and signals with phase shifts by a small amount of time are generated. The power supply voltages of the buffers 502 are controlled by a control voltage, and thereby, the delay times by the buffers may be adjusted. The generated multiphase clock is input to the selector 504.

The selector 504 selects and outputs one phase clock of the multiple clock (S509). Further, the selector 304 selects and outputs one clock signal of the clock signals S109 (S510). The signal S510 selected by the selector 304 is input to the flip-flops 505 and delayed by one clock by the clock S509 with phase shift selected by the selector 504. The delayed signals control the sampling switches 102 of the analog memory part as the clock signals S108 via the buffers 309.

A part of the clock generation part of the example may be shared among the plurality of channels. Specifically, for example, the output clock generation part 507 may use the same clock signal S109 in the respective channels and may be shared among the plurality of channels. Further, the multiphase clock generation part 506 is a circuit that generates a multiphase clock from the reference clock and a necessary function regardless of the delay times of the respective channels, and may be shared among the plurality of channels. The sampling clock generation part 508 sets delay times of the respective channels in the selector 304 and the selector 504. Therefore, the sampling clock generation part is not shared among the channels, but the sampling clock generation parts are provided with respect to each channel. As described above, the circuit is shared among the plurality of channels, and thereby, the area and the power consumption may be reduced.

Figure 6:
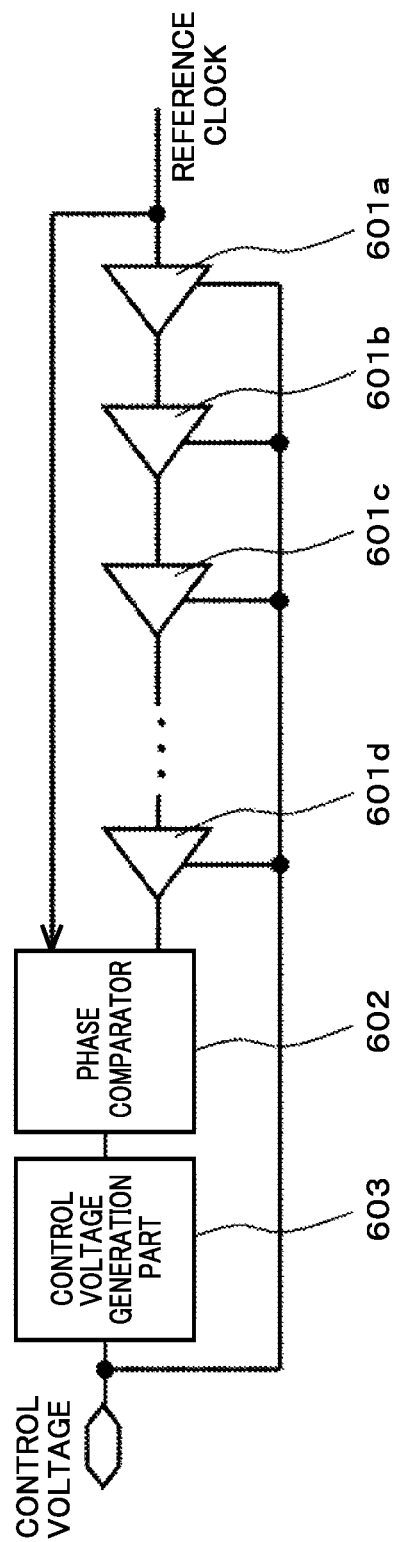
FIG. 6 is a configuration diagram of a DLL circuit according to Example 3 of the invention.

FIG. 6 shows an example of a circuit that determines a control voltage when the multiphase clock is generated according to the example, a Delay Locked Loop (DLL) circuit. The circuit includes buffers 601a, 601b, a phase comparator 602, and a control voltage generation part 603. The reference clock is delayed by the buffers 601 multiple-connected in series. The performance and the number of the buffers are set in advance to values for delays by about one cycle of the reference clock. The outputs of the buffers 601 and the phase of the original reference clock are compared by the phase comparator 602. On the basis of the comparison result, the control voltage is generated by the control voltage generation part 603, the power supply voltages of the buffers 601 are controlled and the delay times by the buffers are adjusted. Note that, not the power supply voltages, but bias currents may be controlled.

In this manner, the phases of the reference clock and the delayed clock are compared by the phase comparator and the delay times by the buffers are controlled, and thereby, an accurate multiphase clock may be generated. Thus obtained control voltage is used as the control voltage of the multiphase clock generation part 506. Note that the buffers 601 within the DLL circuit may be used in common with the buffers 502 of the multiphase clock generation part 506. The reference clock is input to the buffers 601 within the DLL circuit and controlled by the control signal as an output of the control voltage generation part. Further, the reference clock is also input to the buffers 502 of the multiphase clock generation part 506 and controlled by the control voltage. Therefore, these buffers 601 and buffers 502 may be used in common. As a specific circuit configuration, the phase comparator 602 and the control voltage generation part 603 are series-connected to the outputs of the buffers 502 of the multiphase clock generation part 506, and the output of the control voltage generation part 603 is used as the control voltage of the buffers 502. In this manner, the circuit may be used in common and the area and the power consumption may be reduced.

Figure 7:
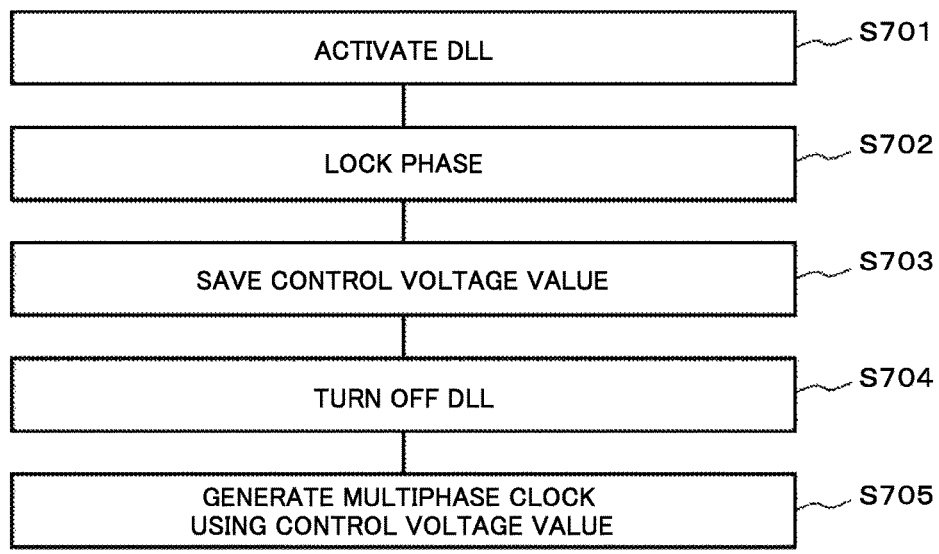
FIG. 7 is a sequence chart for operating the DLL circuit according to Example 3 of the invention.

FIG. 7 shows a sequence for operating the DLL circuit. First, the DLL circuit is activated using a control signal from the outside as a trigger (S701). The DLL is operated, and then, the phase is locked (S702). The phase is locked, and then, the control voltage value at the time is saved (S703). The control voltage value is saved, and then, the power supply of the DLL circuit itself is interrupted (S704). A multiphase clock is generated using the saved control voltage value (S705). As described above, the power supply of the DLL circuit is interrupted after the control voltage is determined, and thereby, power consumption may be suppressed.

As the time when the DLL is activated, the time when the ultrasonic imaging apparatus is activated, the time when the mode of imaging is changed, the time when the temperature changes, or the like is conceivable.

Example 4

The circuit configuration of accumulating analog signals in capacities grounded with respect to the ground has been explained as an analog memory, but the configuration is not limited to that. A circuit configuration of charging the capacities with respect to the virtual ground of the operational amplifier, not the ground, differentiation, not the single end, or providing a reset period is conceivable. Further, not the open-loop circuit, but a closed-loop circuit is used, and thereby, accuracy of the output voltage can be improved.

Figure 8:
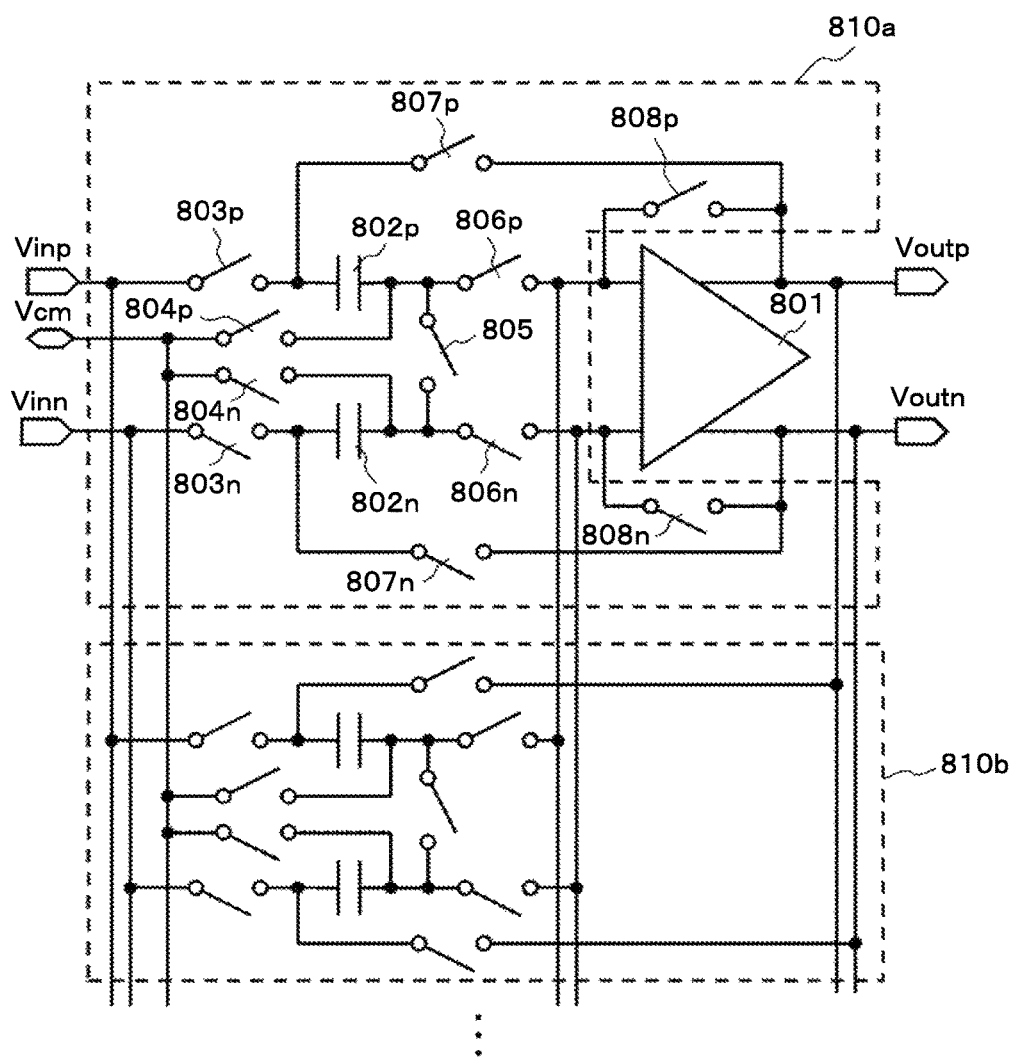
FIG. 8 is a configuration diagram of an analog memory part according to Example 4 of the invention.

FIG. 8 shows a circuit configuration of an analog memory part according to Example 4 of the invention. The part includes an operational amplifier 801 and switch/capacity parts 810a, 810b, .... The switch/capacity parts include capacities 802p, 802n and switches 803p, 803n, 804p, 804n, 805, 806p, 806n, 807p, 807n, 808p, 808n. Here, the indices p, n show the positive side and the negative side of a differential circuit, and are omitted when not particularly necessary.

Figure 9A:
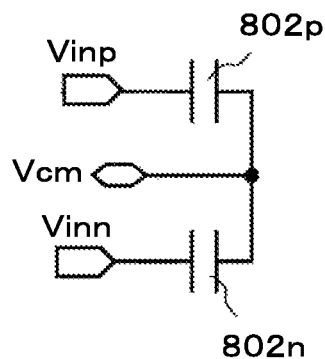
FIG. 9A is an equivalent circuit at sampling of the analog memory part according to Example 4 of the invention.
Figure 9B:
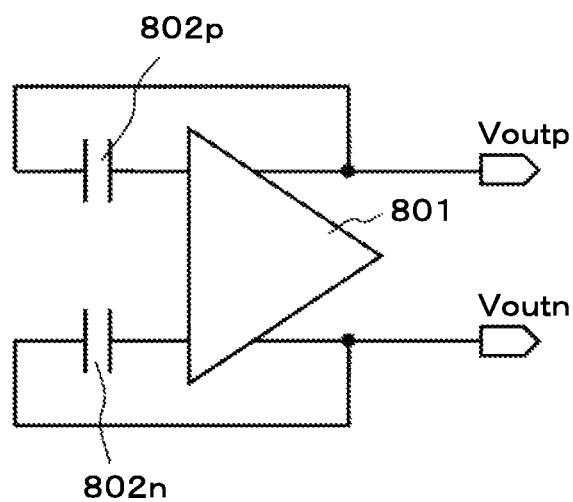
FIG. 9B is an equivalent circuit at holding of the analog memory part according to Example 4 of the invention.

The circuit has the plurality of switch/capacity parts arranged in parallel, and performs sampling and accumulation and, after a predetermined delay time, outputs. Input signals are input as differential signals Vinp, Vinn. FIG. 9A shows an equivalent circuit at sampling of the analog memory according to Example 4 of the invention. Further, FIG. 9B shows an equivalent circuit at holding.

At sampling, the switches 803, 804, 805 are turned on and the switches 806, 807 are turned off. Therefore, the capacities 802 are connected between the input differential signals and Vcm as a common voltage. At sampling, charge corresponding to the input differential signals is accumulated in the capacities 802. At holding, the switches 803, 804, 805 are turned off and the switches 806, 807 are turned on. The capacities 802 and the operational amplifier 801 form feedback circuits and signals corresponding to the charge accumulated in the capacities 802 at sampling are output as differential signals Voutp, Voutn.

The time when the signals accumulated in the capacities 802 at sampling are determined is the time when the switch 805 is turned off. Therefore, the phase of the clock for determining the time when the switch 805 is turned off is changed, and thereby, a small delay time may be generated. At holding, the signals accumulated in the capacities 802 are output while the switches 806 and the switches 807 are on. In the downstream circuit, sampling is performed immediately before the switches 806 and the switches 807 are turned from on to off.

Figure 9C:
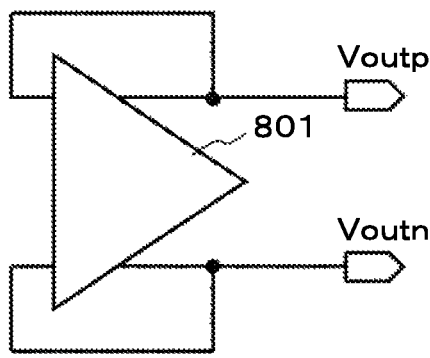
FIG. 9C is an equivalent circuit at resetting of the analog memory part according to Example 4 of the invention.

Further, the switches 808 are used at resetting. FIG. 9C shows an equivalent circuit at resetting. The switches 808 are turned on and the input and the output of the operational amplifier are connected, and thereby, the output signal may be reset at the common-mode voltage. Or, the voltage at the time is held, and thereby, the input offset voltage of the operational amplifier may be cancelled.

As in the example, the differential circuits are used, and thereby, the analog input signals may be accurately sampled and delayed. Particularly, distortion may be suppressed by the differential circuits. Further, the closed-loop circuit using the operational amplifier is formed and the sampled signals are held, and thereby, high-accuracy signals may be obtained. Furthermore, the delay times are provided for the clock signals for controlling the switches, and thereby, the analog signals may be delayed. The delay times of the clock signals are controlled by varying phase, and thereby, delay times with higher resolution may be obtained.

Example 5

Figure 10:
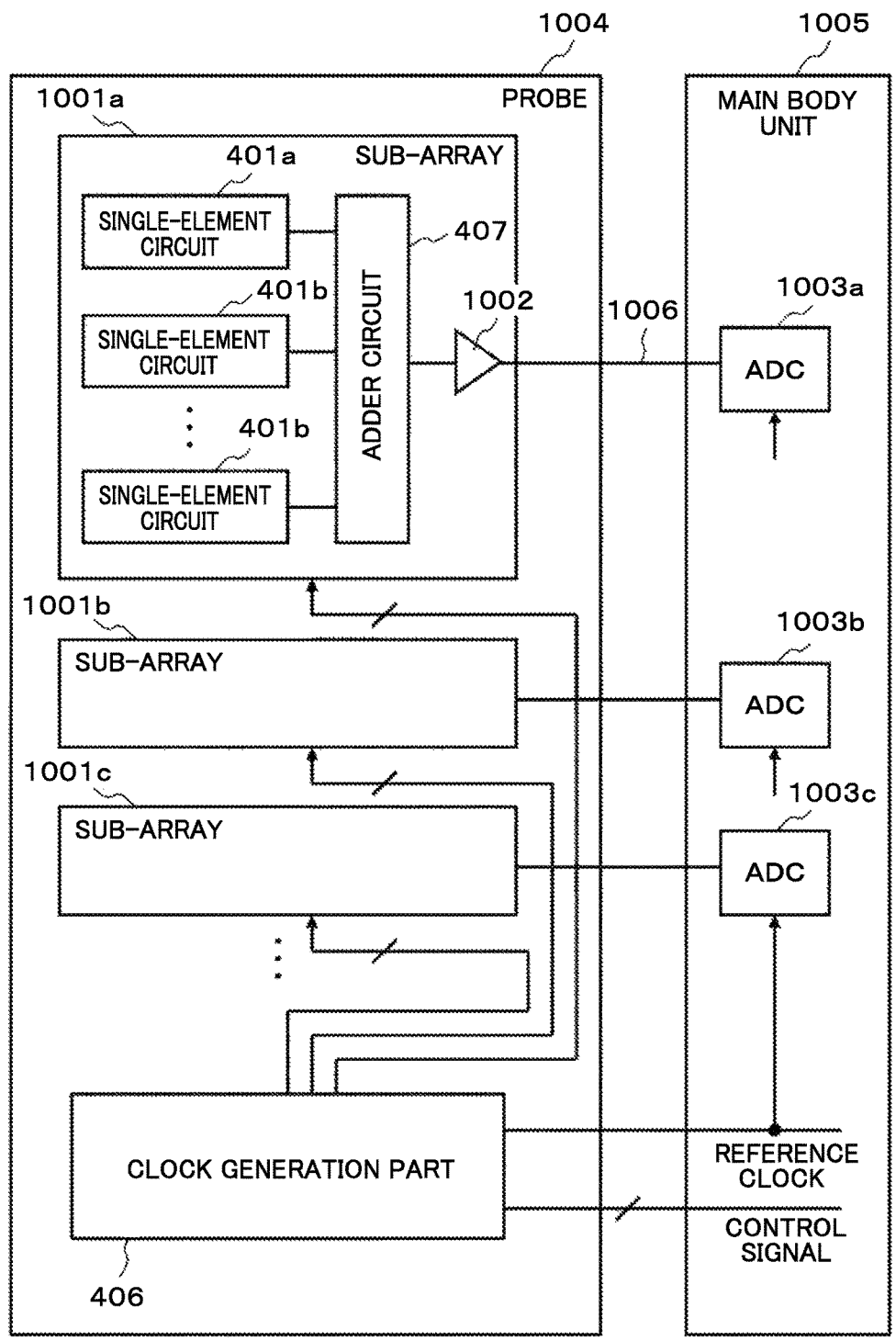
FIG. 10 is a configuration diagram of an ultrasonic imaging apparatus according to Example 5 of the invention.

An ultrasonic imaging apparatus according to Example 5 of the invention is explained using FIG. 10. FIG. 10 is a configuration diagram of the ultrasonic imaging apparatus according to the example. The apparatus includes a probe 1004, a main body unit 1005, and cables 1006. The probe has sub-arrays 1001a, 1001b, . . . and the clock generation part 406. The sub-array includes a plurality of single-element circuits 401a, 401b, . . . , the adder circuit 407, and a buffer 1002. The main body unit has a plurality of ADCs 1003a, 1003b, . . . .

Within the sub-array 1001, ultrasonic wave is transmitted from the respective channels 401 and reflected wave is received. The outputs of the respective channels are added by the adder circuit 407 and transmitted to the main body unit 1005 via the buffer 1002. Within each channel circuit, the received signal is delayed. A clock that sets the delay time is set in the clock generation part 406 based on the reference clock and the control signal from the main body unit 1005.

In the main body unit, the signals from the probe are converted into digital signals in the analog/digital converters (ADCs) 1003. For the clocks used for sampling of the ADCs 1003, the reference clock transmitted from the main body unit 1005 to the probe 1004 is used. The outputs of the delay circuits of the respective channel circuits of the sub-arrays are output in synchronization with the reference clock, and digital conversion is performed in the ADCs in synchronization with the reference clock. Note that, when necessary, a clock obtained by multiplication or division of the reference clock may be used. Or, the phase for analog/digital conversion may be shifted in consideration of the delay time in the cable.

In the delay circuit within the probe, a signal is output in synchronization with the reference clock. Therefore, spike-like noise is generated at the time of rising and falling of the clock. The sampling is performed in the ADCs on the main body unit side in synchronization with the reference clock, and thereby, digitization may be performed while avoiding the noise at the clock edges. Signal processing such as digital phasing is performed on the signals digitized by the ACDs 1003, and thereby, an ultrasonic image is displayed.

The delay circuits and the adder circuits are provided within the probe as in the example, and thereby, the number of wired cables, the number of ADCs may be reduced and the lower cost may be realized.

The invention achieved by the inventors has been specifically explained based on the embodiments, however, obviously, the invention is not limited to the above described embodiments, but various changes can be made within the scope thereof.

REFERENCE SIGNS LIST 101a, 101b, 101c . . . capacity
102a, 102b, 102c . . . switch
103a, 103b, 103c . . . switch
104 . . . buffer
105 . . . clock generation part
106 . . . phase delay control part
107 . . . clock unit delay control part
110 . . . analog memory part
301 . . . pulse generation part
302a, 302b . . . delay element
303a, 303b . . . buffer
304 . . . selector
305a, 305b . . . buffer
306a, 306b . . . buffer
307 . . . selector
308a, 308b . . . delay element
309a, 309b . . . buffer
401a, 401b . . . single-element circuit
406 . . . clock generation part
407 . . . adder circuit
402 . . . transducer
403 . . . transmitting part
404 . . . transmission/reception separating part
405 . . . receiving analog front end part
501a, 501b . . . flip-flop (FF)
502a, 502b . . . buffer
503a, 503b . . . buffer
504 . . . selector
505a, 505b . . . flip-flop
506 . . . multiphase clock generation part
507 . . . output clock generation part
508 . . . sampling clock generation part
601a, 601b . . . buffer
602 . . . phase comparator
603 . . . control voltage generation part
801 . . . operational amplifier 810a, 810b . . . switch/capacity part
802p, 802n . . . capacity
803p, 803n, 804p, 804n, 805, 806p, 806n, 807p, 807n, 808p, 808n . . . switch
1004 . . . probe
1005 . . . main body unit
1006 . . . cable
1001a, 1001b . . . sub-array
1002 . . . buffer
1003a, 1003b . . . ADC

The invention claimed is:

1. A delay circuit comprising:
an input line to which an analog input signal is input;
a plurality of analog signal memory devices;
an output line from which an analog output signal is output;
a plurality of sampling switches that control connection/disconnection between the input line and one of said plurality of analog signal memory devices;
a plurality of output switches each of which controls connection/disconnection between one of said plurality of analog signal memory devices and the output line; and
a clock generator that generates sampling switch control signals for respectively controlling the plurality of sampling switches and output switch control signals for respectively controlling the plurality of output switches from a reference clock,
wherein the clock generator comprises
a plurality of series-connected buffer circuits; and
a first selector configured to select one signal from respective outputs of the plurality of buffer circuits,
wherein a plurality of signals with different phase are generated with respect to the phase of the reference clock by the buffer circuits,
wherein a phase delay signal of single phase of the plurality of signals with different phase is selected by the first selector, and
wherein the sampling switch control signal is generated based on the phase delay signal,
wherein the delay circuit is configured to delay signals by controlling the plurality of sampling switches to accumulate the analog input signal in the plurality of analog signal memory devices and controlling the plurality of output switches to output the signals accumulated in the plurality of analog signal memory devices to the output line, and
wherein a phase of the plurality of sampling switch control signals is shifted with respect to a phase of the plurality of output switch control signals based on an accumulated charge stored using the plurality of analog signal memory devices.

2. The delay circuit according to claim 1,
wherein the clock generator includes a clock unit delay controller that sets delays in units of clock cycles and a phase delay controller that sets phase delays with phase shifts of a clock,
wherein a delay time between the output switch control signal and the sampling switch control signal is a total of a phase delay with a phase shift of the reference clock and a delay in units of clock cycles of an integral multiple of a cycle of the reference clock.

3. The delay circuit according to claim 1, wherein a relationship between a phase of the reference clock and a phase of the output switch control signal is a fixed value.

4. The delay circuit according to claim 1, further comprising a first plurality of series-connected delay elements,
wherein the phase delay signal is used as a clock input to the first plurality of series-connected delay elements, and
output signals of the first plurality of series-connected delay elements are used for the plurality of sampling switch control signals.

5. The delay circuit according to claim 1, further comprising:
a phase comparator that compares phase of two signals; and
a control voltage generator that generates a control voltage based on an output of the phase comparator,
wherein a signal input to the plurality of buffer circuits is the reference clock,
wherein an output signal at a final stage of the plurality of buffer circuits and the phase of the reference clock are compared by the phase comparator, and
wherein delay times of the plurality of buffer circuits are controlled based on the control voltage as an output of the control voltage generator.

6. The delay circuit according to claim 5, further comprising a control voltage holding circuit that holds the control voltage,
wherein when the phase comparator and the control voltage generator are operated, the control voltage is held in the control voltage holding circuit, and
wherein the phase comparator and the control voltage generator are transition to a lower power consumption state based on the control voltage held in the control voltage circuit.

7. The delay circuit according to claim 1, further comprising:
a pulse generator that generates pulse by dividing the reference clock;
a second plurality of series-connected delay elements; and
a second selector that selects one of outputs of the second plurality of series-connected delay elements,
wherein the second plurality of series-connected delay elements generate signals delayed by predetermined clock cycles, and
wherein the signal selected by the second selector is input to the buffer circuits.

8. The delay circuit according to claim 1, further comprising:
a pulse generator that generates pulse by dividing the reference clock;
a second plurality of series-connected flip-flop circuits, to which the reference clock and an output of the pulse generation part are input, that generate signals delayed by predetermined clock cycles;
a second selector that selects one of outputs of the second plurality of flip-flop circuits; and
a first plurality of series-connected flip-flop circuits,
wherein the phase delay signal and an output of the second selector are input to the first plurality of flip-flop circuits, and output signals of the first plurality of flip-flop circuits are used for the plurality of sampling switch control signals.

9. The delay circuit according to claim 1, wherein the analog signal memory device is a capacitor.

10. An electronic circuit comprising:
a plurality of input lines to which an analog input signal is input;
a plurality of analog signal receiving circuits each respectively connected to one of the plurality of input lines;

a plurality of output lines each output from a respective one of said plurality of analog signal receiving circuits; and a clock generator, wherein each of the analog signal receiving circuits comprises a plurality of analog signal memory devices;

a plurality of sampling switches each of which controls connection/disconnection between the input lines and one said analog signal memory device; and a plurality of output switches each of which controls connection/disconnection between the output lines and one said analog signal memory device, wherein the clock generator generates sampling switch control signals for respectively controlling the plurality of sampling switches and output switch control signals for respectively controlling the plurality of output switches of each of the plurality of analog signal receiving circuits based on a reference clock, wherein the clock generator comprises a plurality of series-connected buffer circuits; and a first selector configured to select one signal from respective outputs of the plurality of buffer circuits, wherein a plurality of signals with different phase are generated with respect to the phase of the reference clock by the buffer circuits, wherein a phase delay signal of single phase of the plurality of signals with different phase is selected by the first selector, and wherein the sampling switch control signal is generated based on the phase delay signal, wherein a delay time between the output switch control signal and the sampling switch control signal is a total of a phase delay with a phase shift of the reference clock and a delay in units of clock cycles of an integral multiple of a cycle of the reference clock, wherein a relationship between phase of the output switch control signal and phase of the reference clock is a fixed value, and wherein output signals of each of the plurality of analog signal receiving circuits are output in synchronization with the reference clock.

11. The electronic circuit according to claim 10, further comprising an adder circuit that adds signals of the plurality of output lines, wherein the signals of the plurality of output lines are synchronized and added in the adder circuit.

12. The electronic circuit according to claim 11, further comprising a filter that removes a signal at a frequency of the reference clock, wherein the filter is connected to the plurality of output lines, and output signals of the analog signal receiving circuits are filtered.

13. The electronic circuit according to claim 11, further comprising an analog/digital converter that converts an analog signal into a digital signal, wherein an output of the adder circuit is input to the analog/digital converter, and a time when the analog signal is converted into the digital signal by the analog/digital converter is generated from the reference clock.

14. An ultrasonic imaging apparatus comprising:

a plurality of ultrasonic transducers that transmit and receive ultrasonic signals;

a plurality of input lines to which respective received signals of the plurality of ultrasonic transducers are input;

a plurality of analog signal receiving circuits each respectively connected to one of said plurality of input lines;

a plurality of output lines each output from a respective analog signal receiving circuit;

an adder circuit that adds signals of the plurality of output lines; and a clock generator, wherein each of the analog signal receiving circuits comprises a plurality of analog signal memory devices;

a plurality of sampling switches each of which controls connection/disconnection between the input lines and one of said plurality of analog signal memory devices; and a plurality of output switches each of which controls connection/disconnection between one of the plurality of analog signal memory devices and the output lines, wherein the clock generator generates sampling switch control signals for respectively controlling the plurality of sampling switches and output switch control signals for respectively controlling the plurality of output switches of each of the plurality of analog signal receiving circuits based on a reference clock, wherein the clock generator comprises a plurality of series-connected buffer circuits; and a first selector configured to select one signal from respective outputs of the plurality of buffer circuits, wherein a plurality of signals with different phase are generated with respect to the phase of the reference clock by the buffer circuits, wherein a phase delay signal of single phase of the plurality of signals with different phase is selected by the first selector, and wherein the sampling switch control signal is generated based on the phase delay signal, wherein a delay time between the output switch control signal and the sampling switch control signal is a total of a phase delay with a phase shift of the reference clock and a delay in units of clock cycles of an integral multiple of a cycle of the reference clock, wherein a relationship between a phase of the output switch control signal and a phase of the reference clock is a fixed value, wherein output signals of each of the plurality of analog signal receiving circuits are output in synchronization with the reference clock, and wherein the signals of the plurality of output lines are synchronized and added in the adder circuit.

* * * * *